United States Patent [19]

Schlesinger

[11] 4,283,498

[45] Aug. 11, 1981

[54] BIOLOGICAL SPECIMEN COLLECTION AND TRANSPORT SYSTEM

[76] Inventor: Joseph D. Schlesinger, 1013 Sunset Pl., Ojai, Calif. 93023

[21] Appl. No.: 89,603

[22] Filed: Oct. 29, 1979

[51] Int. Cl.³ .............................................. C12M 1/24
[52] U.S. Cl. .................................... 435/296; 435/299; 435/810
[58] Field of Search .................. 435/30, 31, 292, 293, 435/294, 295, 296, 297, 298, 299, 300, 301, 800, 810; 206/63.3, 440, 365

[56] References Cited

U.S. PATENT DOCUMENTS

| | | | |
|---|---|---|---|
| 2,218,002 | 10/1940 | Hamilton | 4/258 |
| 2,835,246 | 5/1958 | Boettger | 128/2 |
| 2,874,091 | 2/1959 | Fisk | 435/810 X |
| 3,440,144 | 4/1969 | Andersen | 435/810 X |
| 3,518,164 | 6/1970 | Andelin et al. | 435/296 X |
| 3,655,515 | 4/1972 | Noorlander | 435/294 X |
| 3,711,378 | 1/1973 | Kereluk | 435/810 X |
| 3,968,012 | 7/1976 | Jones | 435/810 X |
| 4,014,748 | 3/1977 | Spinner et al. | 435/810 X |
| 4,038,148 | 7/1977 | Miller et al. | 435/810 X |

Primary Examiner—Robert J. Warden
Attorney, Agent, or Firm—Christie, Parker & Hale

[57] ABSTRACT

A biological specimen collection and transport apparatus is provided which is especially useful for collection of sputum. The system includes a hollow specimen collection receptacle which is readily centrifuged. A funnel which has a discharge tube extending into the specimen receptacle is provided for ease of collection of the specimen. The funnel and receptacle are supported by a base. There is also provided an outer protective covering which is flexible and transparent and which coaxially encloses the specimen receptacle and is attached to the funnel. The flexible outer protective covering maintains the exterior of the hollow specimen receptacle free from contamination from the specimen during the specimen collection process. A screw cap is additionally provided and is removably attached to the specimen receptacle for sealing the specimen receptacle.

33 Claims, 6 Drawing Figures

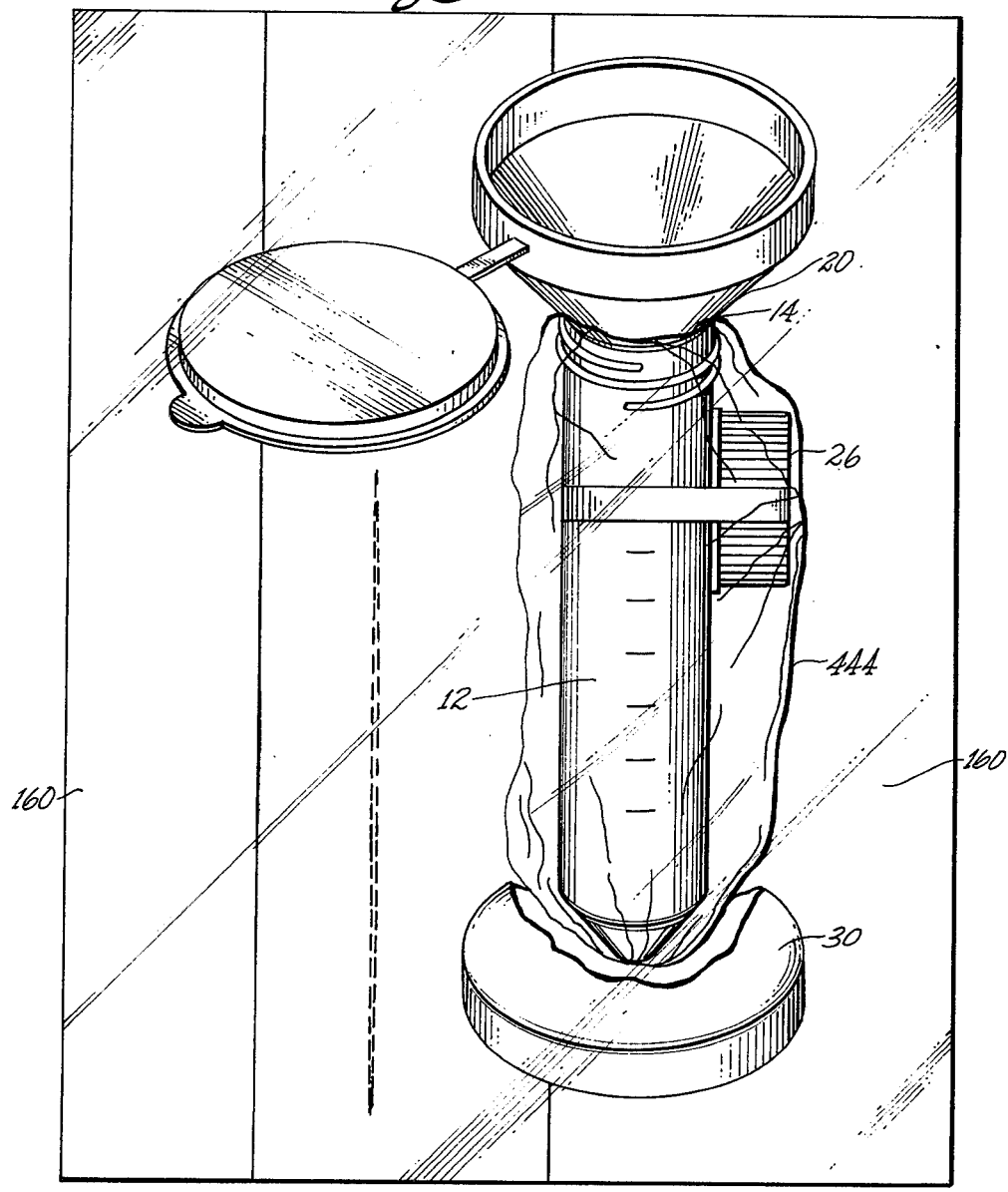

BIOLOGICAL SPECIMEN COLLECTION AND TRANSPORT SYSTEM

BACKGROUND OF THE INVENTION

Biological specimens such as blood, urine, sputum, and the like are routinely collected in the home, in hospitals, in doctor's offices, and in laboratories using a variety of devices having various configurations and shapes.

It is important that, during the handling and testing of the biological specimens collected, infection is not spread. For instance, it can be important when collecting sputum specimens in cases of bacterial pneumonia, bronchiectasis mycosis and other pulmonary infections that the outside of a specimen container be free of contamination from the specimen. Having the outside of the specimen container remain free of contamination will enhance the probability that an individual handling the container, such as a laboratory technician, will not become infected or spread the infection.

U.S. Pat. No. 2,218,002 to Hamilton discloses a device for the collection of sputum. When in use, however, it can be seen that a patient can contaminate the outer wall of the cup body with sputum and this contamination can thereafter be transmitted to an individual who subsequently handles the cup.

U.S. Pat. No. 2,835,246 to Boettger discloses a device for handling medical specimens which consists of an inner and outer container. The sample is collected in a inner container and the inner container is thereafter inserted into the outer container. The outside surface of the inner container can, therefore, be contaminated during the collection process.

Additionally, it is desirable to provide a simple and inexpensive system for the collection of biological specimens and systems such as those disclosed by Boettger appear to be complex and expensive.

Further, it is desirable to provide a container for collection of a specimen in which the specimen can be directly analyzed. This can eliminate the requirement for the specimen to be transferred to another container prior to analysis. For example, it is desirable to collect a specimen in a tube or the like which can be directly centrifuged so that the specimen need not be transferred to a centrifuge tube for analysis. By eliminating the transfer step, the safety of handling of the container having the sample therein is enhanced.

Although U.S. Pat. No. 3,518,164 to Andelin et al discloses a sputum collection system which includes a tube, i.e., a specimen receptacle, which can be centrifuged, it additionally discloses an outer protective body which is made of a rigid material which coaxially encloses a specimen receptacle. The other protective body is provided to support the specimen receptacle in a vertical position. Having a rigid outer protective body as disclosed by Andelin can be expensive and, additionally, can add to the complexity of using such a sputum collection system.

It is desirable, therefore, to provide a biological specimen collection and transport apparatus that is manufactured of lightweight materials to enhance economics of manufacturing and transportation, is simple to use, and enhances prevention of the spread of infection during transportation and analysis of a collected specimen.

SUMMARY OF THE INVENTION

There is provided a biological specimen collection and transport apparatus which comprises an elongated, hollow specimen receptacle having a closed bottom end and an open top end. The specimen collection apparatus further comprises a detachable conduit means mounted on the open top end of the hollow specimen receptacle for introducing a biological specimen into said receptacle. A base means for receiving the closed bottom end of the specimen receptacle is provided to support the specimen receptacle in a vertical position. There is also provided a flexible outer protective covering which encloses the outer surface of the elongated specimen receptacle and prevents contamination of the outer surface of the receptacle by a biological specimen during introduction of the specimen into the receptacle. Additionally, means is provided for attaching the flexible outer protective covering to the detachable conduit means.

DRAWINGS

These and other features, aspects, and advantages of the present invention will become better understood with reference to the following description, appended claims, and accompanying drawings wherein:

FIG. 6 is a perspective view of yet another preferred embodiment of the biological specimen collection and transport apparatus provided in accordance with this invention.

DETAILED DESCRIPTION

This invention relates to an apparatus used for collecting and transporting a biological specimen. More particularly, this invention relates to a low cost biological specimen collection and transport apparatus which enhances hygiene during collection and evaluation of said specimen.

Figure 1:
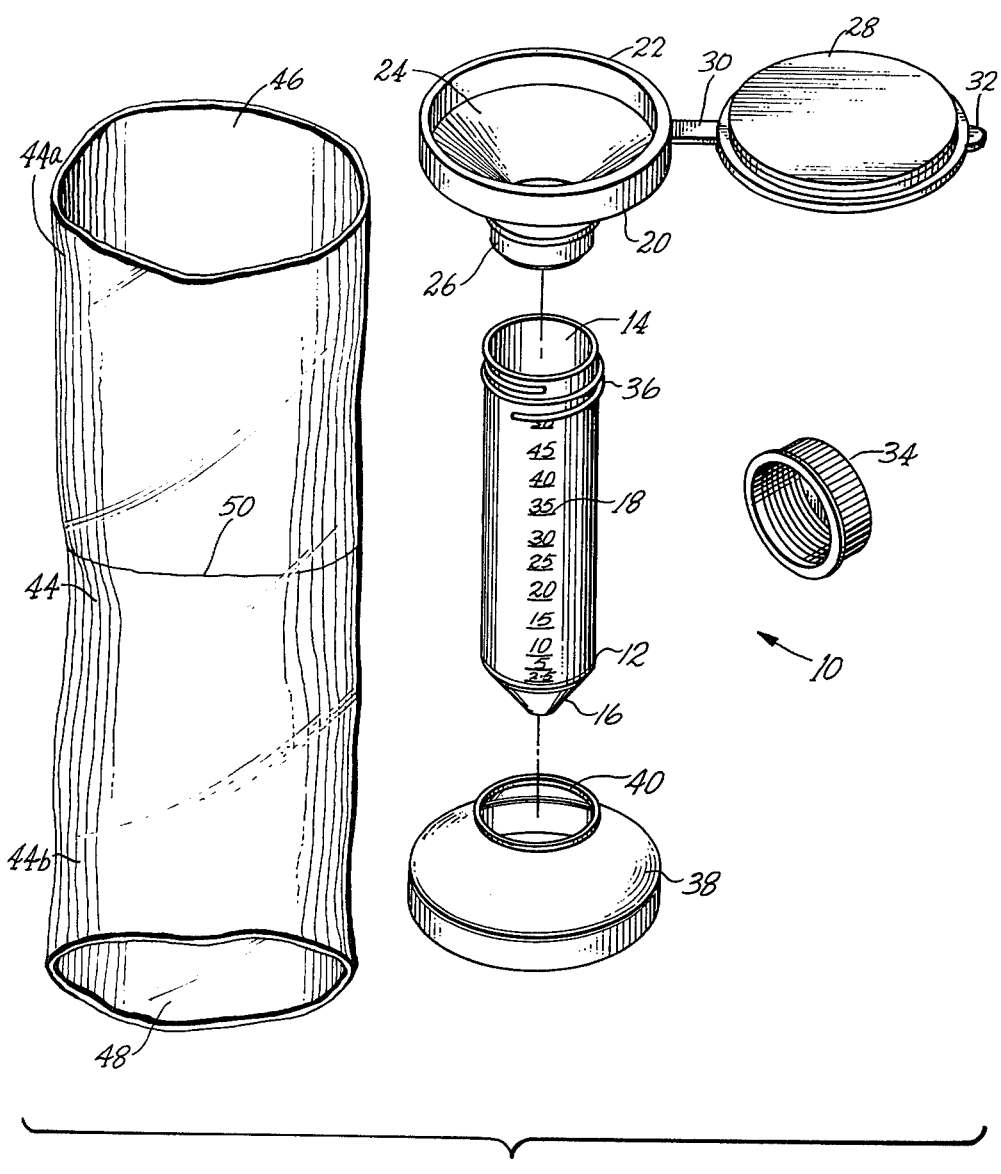
FIG. 1 is an exploded perspective view of a biological specimen collection and transport apparatus provided in accordance with this invention.

Referring to FIG. 1, there is shown an exploded perspective view of a biological specimen collection and transport apparatus 10 useful in practice of principles of this invention.

An elongated, cylindrical, hollow specimen receptacle 12 is provided for collection of the biological specimen. The specimen receptacle 12 has an open end 14 at the top and a closed conically shaped end 16 at the bottom.

It is desirable that the hollow specimen receptacle provided is transparent or at least translucent so that the level of a specimen collected in the receptacle can be visually observed through the sides of the receptacle.

For example, the receptacle can be molded of a plastic material such as polypropylene, polyethylene, polystyrene, or the like. Additionally, the receptacle can be made of clear or frosted glass. It is preferred, however, that the specimen receptacle be made of plastic so that after evaluation of a specimen, the hollow specimen receptacle having the specimen contained therein can be readily disposed of, for example, by incineration or the like. This can provide for hygienic disposal of the specimen without having to be concerned about sterilizing the receptacle for re-use, as could be the case when a non-disposable receptacle such as glass is provided.

It is also desirable that the collected specimen need not be transferred from an original receptacle to a diagnostic test tube or centrifuge tube or the like prior to analysis. When a specimen does not have to be transferred from one container to another, the safety of the process is enhanced because there is a reduced risk of spreading infection by an individual handling the collected specimen.

Therefore, a receptacle having a size and shape which is readily adaptable to fit into standard centrifuges is preferred.

It is also desirable to provide a receptacle that has a graduated scale of reference numerals to indicate the quantity of the specimen contained therein. The increments, i.e., the size of the graduations, can be as desired.

The hollow specimen receptacle 12 shown in FIG. 1 is a translucent tube molded of polypropylene which has a capacity of about 50 milliliters and has been found to fit readily into standard centrifuges. A graduated scale 18 is provided on the hollow specimen receptacle wherein the graduations are at 2.5, 5, 7.5, and 10 milliliters and at increments of 5 milliliters thereafter up to 50 milliliters. These graduations are provided to aid in establishing the amount of the specimen that has been collected in the specimen receptacle and also to aid in analysis, as described hereinabove.

There is additionally provided a detachable conduit means mounted on the open end of the hollow specimen receptacle 12 for introducing a biological specimen into the hollow specimen receptacle.

In a preferred embodiment, a funnel 20 is provided as the detachable conduit means for introducing the biological specimen into the hollow specimen receptacle 12. The funnel 20 comprises a rim 22 surrounding the top of the funnel, a mouth 24, and a discharge tube 26 which is at the bottom of the funnel and which comprises the base of the funnel. The discharge tube 26 is inserted into and is received within the open end 14 of the hollow specimen receptacle so that the specimen can flow from the mouth of the funnel downwardly through the funnel, and thence through the discharge tube into the specimen collection receptacle without contaminating the outside surface of the collection receptacle.

It is desirable that the discharge tube be sized so that when inserted into the open end of the hollow specimen receptacle, the outer surface of the discharge tube frictionally engages the inner surface of the open top end of the elongated, hollow specimen receptacle to form a press fit.

The funnel, therefore, fits snugly into the specimen receptacle so that when in use the funnel will remain in place under normal handling, e.g., while specimens are deposited into the funnel. If, for example, the discharge tube has an outside diameter much less than the inside diameter of the open end of the specimen receptacle and fits loosely therein, a person depositing a specimen into the funnel can readily tilt the funnel in relation to the specimen receptacle or jar the funnel loose from the receptacle. This can cause a portion of the specimen to flow downwardly, contacting the outside of the receptacle, thereby contaminating the outer surface of said receptacle.

The funnel can be made of plastic or glass or other materials, but is preferably made of a lightweight plastic material. For example, the funnel 20 of the preferred embodiment is molded of polyethylene.

It is preferred that a means be provided for closing the mouth 24 of the funnel. This can be accomplished by providing a funnel lid 28 which fits over the upper surface of the funnel rim 22 and/or forms a pressure fit inside the mouth of the funnel.

The funnel lid 28 can be used for preventing foreign material from entering the specimen receptacle. For example, a specimen can be collected in several discharges and the funnel lid can be opened during each discharge and closed between discharges to prevent entry of foreign matter into the collected specimen.

It is desirable that the funnel lid be attached by a hinge or the like to enhance ease of opening and closing the lid, while preventing the lid from being dropped or lost. The funnel lid 28, as shown in FIG. 1, is formed to seat inside the mouth of the funnel to form a pressure closure. Additionally, the funnel lid 28 is hingedly attached to the funnel by a hinge 30. On the edge of the funnel lid 28, there is provided a lift tab 32 to facilitate opening and closing the funnel lid.

The funnel lid is desirably made of a material that enhances the ease of closing the funnel to form a pressure fit, for example, a plastic material such as polypropylene, polyethylene, polystyrene, or the like can be used as desired.

Additionally, means are provided for sealing the specimen receptacle after the specimen is collected. For example, a cap 34 is provided which fits over the open end of the specimen receptacle for sealing the specimen in the receptacle.

It is desired that the receptacle be provided with threads 36 at its upper open end 14, and that the cap 34 be threaded on the inside for screwing onto the threads 36 of the hollow specimen receptacle to provide a liquid tight fit or seal between the cap and receptacle.

It is desirable to provide such a liquid or pressure fit so that the sample can be transported without spillage. Spillage of the sample prior to analysis can, of course, require that the entire collection process be repeated and also can increase the risk that infection will be spread to others.

Biological samples collected can be transported, for instance, from one location in a hospital to another or can also be sent by mail or the like from a patient at home to a hospital or laboratory for evaluation. It is, therefore, important that during transfer, the specimen does not spill from the hollow specimen receptacle, thereby contaminating the outer surface of the specimen receptacle and enhancing the probability that a laboratory technician or other person handling the receptacle will be contaminated by the specimen.

The cap 34, which is molded of plastic and threaded on the inside, can be removably attached to the specimen receptacle 12 by means of an elastic band, tape, a clip, or the like so that after completion of collection of the specimen, the cap can be readily removed and threaded onto the threaded top portion of said specimen receptacle.

A base means is also provided for receiving the closed bottom end of the elongated, hollow specimen receptacle 12 for supporting the elongated, hollow specimen receptacle in an upright or vertical position.

For example, referring again to FIG. 1, a base 38 comprising a hollow, generally hemispherically shaped enclosure having an opening 40 in the center thereof is provided. The conically shaped bottom portion 16 of the specimen receptacle 12 is inserted through the opening 40 at the upper end of the base so that the specimen receptacle 12 is in frictional engagement with the surface of the base at the opening in the base so that the specimen receptacle is held in a vertical position when so engaged.

The base can be made of a material such as glass or metal, but is preferably made of a plastic, such as polystyrene, polypropylene, polyethylene, or the like. The base 38 comprises polystyrene which is vacuum formed.

A flexible outer protective covering 44 is provided which is used to enhance the hygienic use of the apparatus for collection and transportation of biological specimens.

Additionally, embodiments are provided in practice of principles of this invention, wherein the flexible outer protective covering comprises a means for admitting a sterilizing fluid therethrough, while prohibiting the admission of microorganisms. The flexible outer protective covering, therefore, can provide the means for maintaining sterility of the specimen receptacle. In these embodiments, therefore, the requirement of providing a package or container for enclosing the specimen collection and transport apparatus to maintain sterility is eliminated.

The outer protective covering is preferably made of a material which is not readily permeable to gases and vapors, such as air or water vapor. For example, the outer protective covering can be made of a thin translucent or transparent film of polyethylene or polypropylene or other plastic material.

When the biological specimen collection and transport apparatus is fully assembled, the outer protective covering encloses the outer surface of the specimen collection receptacle. The outer surface of the collection receptacle remains enclosed by the outer protective covering during collection of a biological specimen.

It is preferred, therefore, that the outer protective covering be made of a clear material so that the specimen receptacle can be viewed through the covering. When a clear or transparent outer protective covering is provided, the level or the amount of specimen in the specimen receptacle can be visually ascertained during the collection process.

A flexible outer protective covering provides a means for preventing contamination of the outer surface of the hollow specimen receptacle during the introduction of a biological specimen into the funnel and thence into the hollow specimen receptacle. For example, a specimen which is discharged into the funnel and overflows the funnel will flow down the outer surface of the outer protective covering, but will not pass through the outer protective covering to contact and contaminate the outer surface of the hollow specimen receptacle.

The flexible outer protective covering 44 shown in FIG. 1 comprises a cylindrical sheath of plastic film which is shown open at the top end 46 and at the bottom end 48. At least one opening is initially provided so that elements of the specimen collection and transport apparatus, i.e., the funnel 20, elongated specimen receptacle 12, cap 34, and base 38 can be inserted into the outer protective covering. If desired, an outer protective covering can initially be provided in the form of a plastic bag or the like which is closed at one end and open at the opposite end for insertion of the above mentioned elements of the biological specimen collection and transport apparatus.

The outer protective covering can comprise one or more portions which are joined by at least one preweakened line. The pre-weakened line can comprise a score mark or a series of perforations which are made in the outer protective covering. The score mark and/or series of perforations provide a "tear away" feature to said outer protective covering. By a "tear away" feature, it is meant that when forces are exerted on the other protective covering in a direction generally parallel to the axis of the specimen receptacle, the protective covering will separate at the score mark or along the perforations.

Referring to FIG. 1, the flexible outer protective covering 44 comprises an upper portion designated as 44a and a lower portion designated as 44b which are separated by a score mark 50. The score mark made in the surface of the outer protective covering is transverse to the axis of the outer protective covering and encircles the entire outer protective covering.

Additionally, a means is provided for attaching the flexible outer protective covering 44 to the detachable conduit means, i.e., to the funnel 20. The means for attaching the flexible outer protective covering to the funnel can be, for example, the press fit between the funnel 20 and the upper open end 14 of the specimen receptacle 12. Alternatively, the means for sealing the flexible outer protective covering to the funnel can be a bond provided between the covering and the funnel. The bond can be made, for example, by using adhesives or by heat sealing or the like. It is preferred that the bond provides a hermetic or air tight seal between the flexible outer protective covering and the funnel.

Figure 2:
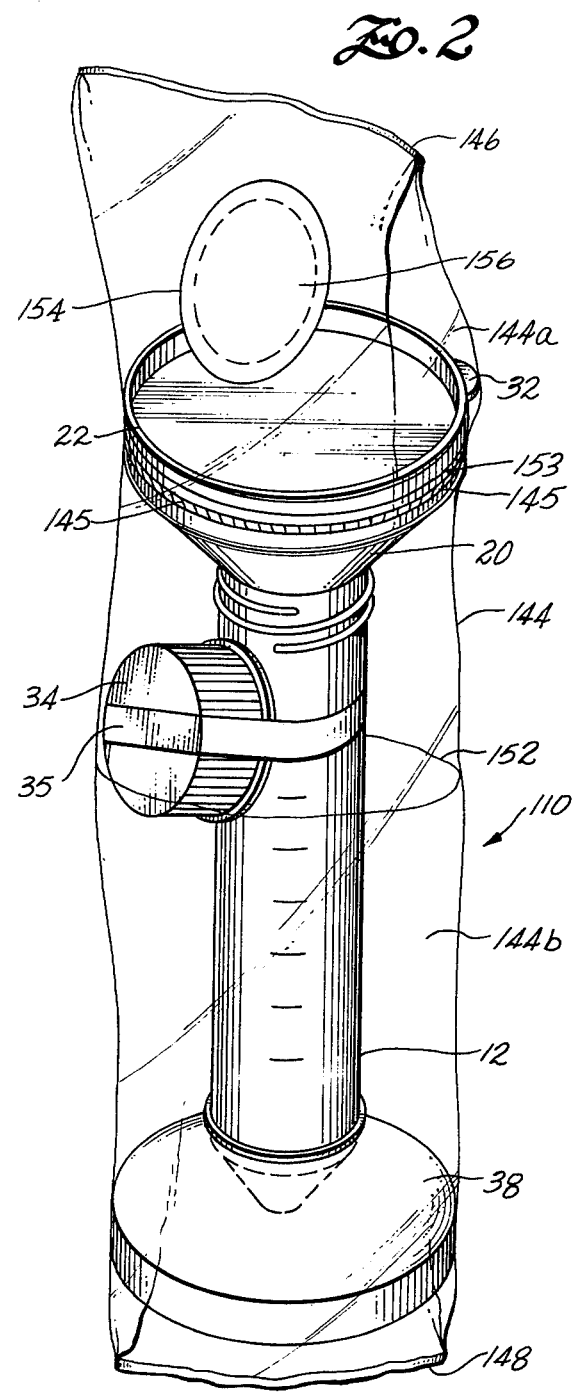
FIG. 2 is a perspective view showing a preferred embodiment of a biological specimen collection and transport apparatus provided in accordance with this invention.

A better understanding of the biological specimen collection and transport apparatus and its method of use can be achieved by referring now to FIG. 2. FIG. 2 shows a preferred embodiment of a fully assembled biological specimen collection and transport apparatus useful in practice of principles of this invention.

In the preferred embodiment, a flexible outer protective covering 144 is provided wherein the outer protective covering encloses elements of the biological specimen collection and transport apparatus 110. For example, the outer protective covering 144 encloses the base 38, the hollow specimen receptacle 12, the cap 34, the funnel 20, and the funnel lid 28.

The flexible outer protective covering 144 comprises a polyethylene film about 2 mils thick sealed at the bottom end 148 and initially open at the top end 146 prior to full assembly of the apparatus 110. Other thicknesses of film can be used as desired to provide a desirable balance of strength of the outer protective covering versus manufacturing cost. After the funnel, funnel lid, hollow specimen receptacle, base, and cap are assembled and inserted into the outer protective covering, the top end 146 is closed by heat sealing or the like. The cap 34 is removably attached to the specimen collection receptacle 12 by a band 35. The band surrounds the cap and specimen receptacle and is made of a plastic material.

The outer protective covering 144 is attached and sealed to the outer surface of the funnel 20 by a bond as shown by bond line 145 which surrounds the entire circumference of the funnel. The bond provides a hermetic seal between the flexible outer protective covering 144 and the funnel 20 and can be made by using adhesive or the like, but is preferably made by heat sealing the outer protective covering to the funnel.

A first score mark 152 is shown made in the surface of the outer protective covering 144, wherein the score mark encircles the flexible outer protective covering 144 and is generally transverse to the axis of the hollow specimen receptacle 12. The first score mark 152 is located between the funnel and the base about midway between the funnel and the base.

There is additionally provided a second score mark 153 located below the top of the funnel, just below the rim 22 of the funnel, but above the bond line 145. The second score mark is similar to the first score mark in that the second score mark is generally transverse to the axis of the hollow specimen receptacle and encircles the entire outer protective covering.

The score mark provided can be formed about 1 mil deep into the 2 mil thick polyethylene film leaving therefore about 1 mil thickness of polyethylene at such a score mark. The amount of film left at such a score mark can be as desired to provide for the desired ease of separation of the outer covering at the score mark.

As described hereinabove, the outer protective covering can comprise means for admitting a sterilizing fluid such as ethylene oxide gas, while prohibiting admission of microorganisms.

For example, in the preferred embodiment, a "sterilization patch" 154 is provided which is bonded at its edges to the outer protective covering and covers a hole 156 formed in the outer protective covering.

The "sterilization patch" referred to herein comprises a semi-permeable membrane which can be made of paper such as a filter paper or the like which can allow passage of gases such as ethylene oxide for sterilization, but which prohibits passage of microorganisms such as bacteria and the like. A sterilization patch can be round, oval, or rectangular, or can be provided in any other shape as desired in order to cover the hole formed in the outer protective covering.

It is preferred that the sterilization patch is impregnated with a plastic material or the like to enhance heat sealing of the patch to the portion of the outer protective covering surrounding the hole formed therein.

If desired, the sterilization patch can be provided at other locations on the outer protective covering and also more than one sterilization patch can be provided, if desired.

For example, although the sterilization patch of the preferred embodiment is shown on an upper portion 144a of the outer protective covering, a sterilization patch can instead be provided on a lower portion 144b of the outer protective covering. Alternatively, in addition to the sterilization patch 154 provided, which comprises part of the upper portion 144a of the outer protective covering, a second sterilization patch can be provided at a location on the lower portion 144b of the outer protective covering.

Polyethylene film provided as bags having various sizes and shapes and which include semi-permeable membranes such as the sterilization patch described hereinabove are provided by Tower Products, Inc. of Mundilein, Ill.

In other embodiments useful in practice of principles of this invention, where sterilization is not achieved using a gas such as ethylene oxide, no sterilization patch need be provided as part of the flexible outer protective covering and sterilization can be achieved by gamma or beta radiation or the like.

Figure 3:
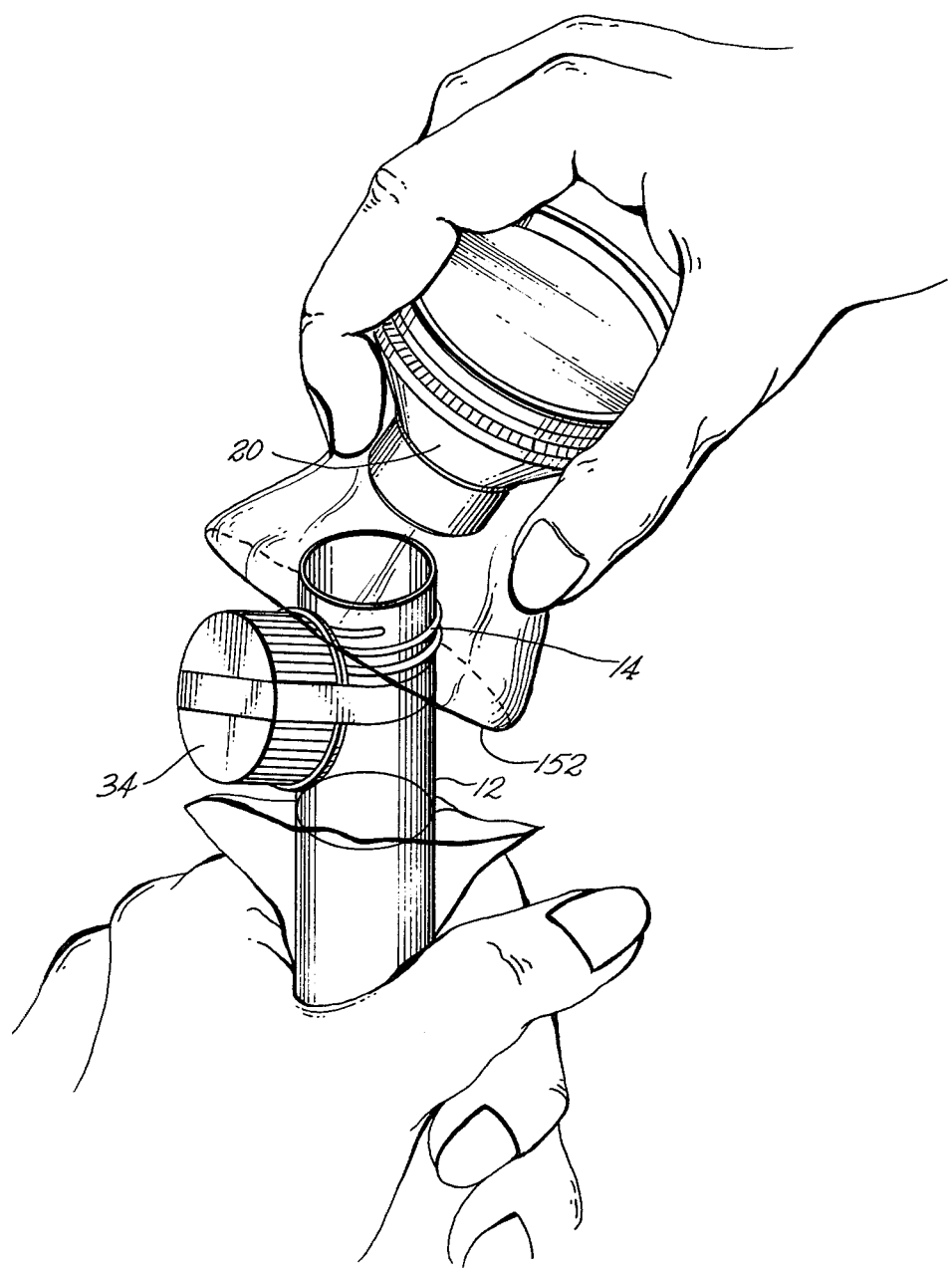
FIG. 3 is a perspective view of the biological specimen collection and transport apparatus as shown in FIG. 2 at one stage during use in accordance with practice of principles of this invention.

Referring again to FIG. 2 and additionally to FIG. 3, an understanding of the method of using the biological specimen collection and transport apparatus of the preferred embodiment can be better understood.

The biological specimen collection and transport apparatus is first held in one hand and the upper portion 144a of the outer protective covering is gripped with the thumb and forefinger of the other hand. A force is exerted on the upper portion 144a of the outer protective covering, thereby causing the outer protective covering to separate at the second score mark 153. This separates the upper portion 144a of the outer protective covering from a lower portion 144b of said outer protective covering and exposes the funnel lid 28. The funnel lid can thereafter be opened by lifting up on the funnel lid tab 32.

The apparatus is now ready for receipt of a biological specimen and, although specimens such as blood, urine, feces, and sputum and the like can be collected, the biological specimen and collection system of this invention is particularly adapted to collection of sputum. The system will, therefore, be described in terms of sputum collection.

A sputum discharge is deposited into the funnel 20, wherein the sputum specimen proceeds downwardly through the discharge tube of the funnel and into the hollow specimen receptacle 12. Generally, when collecting a sputum sample, more than one deposit is made into the funnel. The funnel lid 28 can be closed between each deposit in order to keep foreign substances and the like from contaminating the sputum sample during the collection process, as described hereinabove.

It can be seen that during the process of collecting the sputum sample, the outer surface of the hollow specimen receptacle remains enclosed by the lower portion 144b of the outer protective covering. Therefore, any overflow of sputum from the funnel will flow down the outer surface of the lower portion of the outer protective covering. The sputum, therefore, will not come in contact with either the outer surface of the specimen receptacle 12, the cap 34, or the base 30, which remain enclosed by the lower portion of the outer protective covering.

When the desired level of sputum has been collected, as can be ascertained visually through the outer protective covering and through the side wall of the specimen receptacle, the specimen receptacle is ready for removal from within the lower portion of the outer protective covering.

Referring now to FIG. 3, in order to remove the specimen receptacle, one hand can be used to grip a lower portion of the specimen receptacle which is surrounded by the lower portion of the outer protective covering, and the other hand can thereafter grip the funnel and exert an upward force until the outer protective covering separates at the first score mark 152.

This operation exposes the cap 34 and the threaded open end 14 of the specimen receptacle.

The funnel and the portion of the outer protective covering hermetically sealed to the funnel, which is removed with the funnel, can thereafter be discarded. The cap is then screwed onto the threaded top portion of the specimen receptacle and tightened to provide a liquid seal to maintain the sputum in the specimen receptacle during transport and storage of the sample.

If desired, a label can be provided with the biological specimen collection and transport system and can be affixed to the specimen receptacle after collection of the specimen for identification of said specimen. For convenience, if desired, the label can be removably attached to the hollow specimen receptacle and can be removed with the cap after the outer protective covering is separated at the first score mark 152.

The bottom portion of the outer protective covering surrounding the base 30 can thereafter be discarded and, if desired, the base can also be discarded. Alternatively, the base can be kept for use in maintaining the specimen receptacle in an upright position during analysis.

Figure 4:
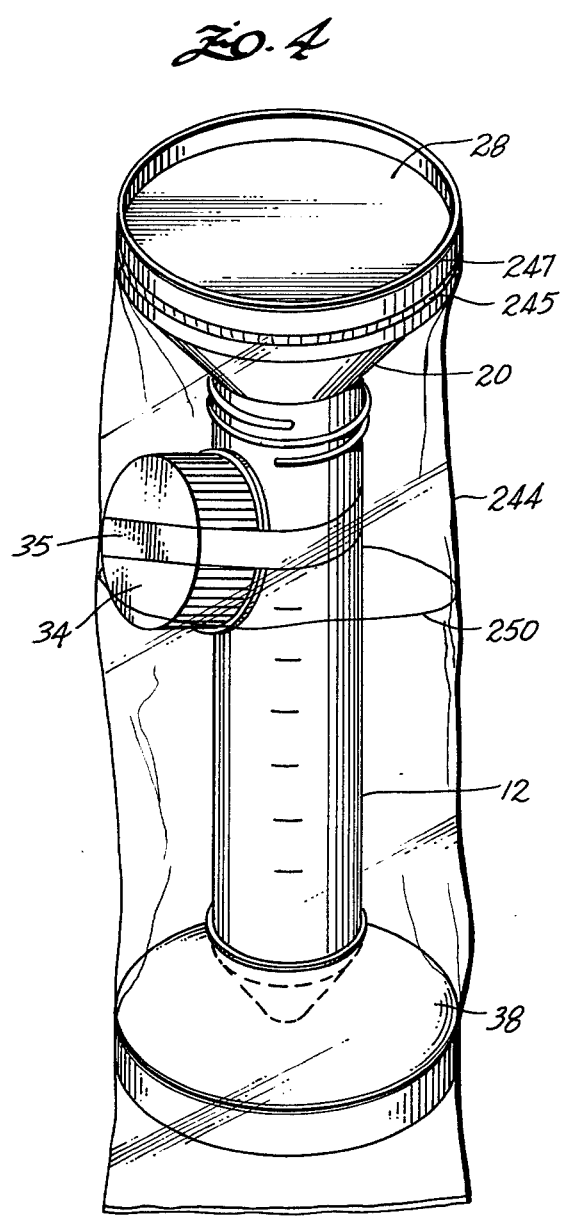
FIG. 4 is a perspective view showing another preferred embodiment of the biological specimen collection and transport apparatus provided in accordance with this invention.

Referring now to FIG. 4, there is shown a perspective view of another preferred embodiment of a fully assembled biological specimen collection and transport apparatus provided in accordance with this invention.

There is provided an outer protective covering 244 which encloses the base 38 and extends upwardly enclosing the specimen receptacle 12 and the cap 34. The cap 34 is removably attached to the specimen receptacle by a plastic band 35. The outer protective covering 244 is hermetically bonded by heat sealing or the like to the funnel 20 as shown by bond line 245.

In order to maintain sterility of the interior of the specimen collection receptacle 12, the funnel lid 28 is sealed to the funnel. This can be accomplished by providing a seal 247 which circumferentially surrounds both the funnel lid and the funnel and provides a hermetic seal between the funnel lid and funnel.

Sterilization can be accomplished by gamma or beta radiation or other means which does not require a sterilizing gas such as ethylene oxide to pass into the interior of the specimen receptacle. Alternatively, although not shown, the outer protective covering 244 can comprise a sterilization patch, as described hereinabove, so that the specimen receptacle 12 can be sterilized by a gas such as ethylene oxide or the like.

In the preferred embodiment, sterility of the interior of the hollow specimen receptacle 12 is maintained by the outer protective covering and by the hermetic seal between the funnel lid and the funnel.

There is a score mark 250 provided on the outer protective covering 244. The score mark is located between the funnel 20 and the base 38 and is similar to the score marks as described in the embodiment shown in FIGS. 2 and 3.

The biological specimen collection and transport apparatus shown in FIG. 4 is used in a similar manner to the apparatus shown in FIGS. 2 and 3. It can be seen, however, that when using the biological specimen collection and transport apparatus, as shown in FIG. 4, wherein the lid 28 is secured to the mouth of the funnel by a hermetic seal, the seal is removed prior to opening the funnel lid in preparation for collection of a specimen.

Figure 5:
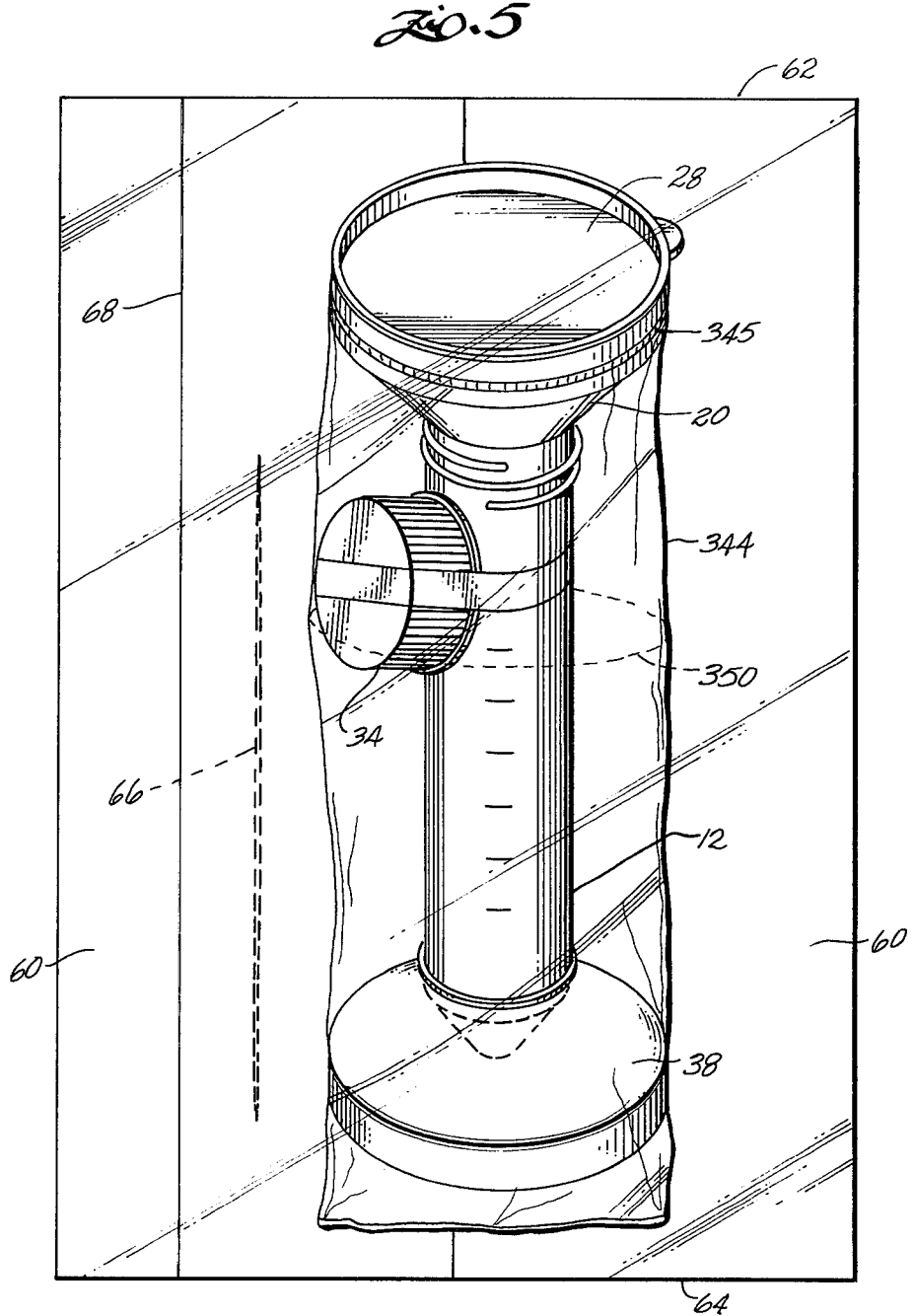
FIG. 5 is a perspective view of another preferred embodiment of the biological specimen collection and transport apparatus provided in accordance with this invention.

Referring now to FIG. 5, there is shown yet another preferred embodiment of the biological specimen collection and transport apparatus of this invention, wherein an outer protective covering 344 is provided to enhance the hygienic handling of the specimen receptacle, but the outer protective covering does not maintain sterility of the inside of the hollow specimen receptacle.

In the preferred embodiment shown in FIG. 5, there is included a specimen collection receptacle 12, a base 38, a cap 34 removably attached to the specimen collection receptacle, a funnel 20, and a funnel lid 28 hingedly attached to the funnel. The outer protective covering 344 has a series of perforations shown as pre-weakened line 350. The perforations 350 extend completely through the outer protective covering, are transverse to the axis of the specimen receptacle 12, and encircle said outer protective covering.

In this embodiment, the outer protective covering encloses the base 38 and extends upwardly coaxially enclosing the specimen receptacle 12. The outer protective covering is bonded by use of adhesives, by heat sealing, or by sonic welding or the like or is attached in some other manner to the funnel 20, either at the outside of the funnel, as shown by bond line 345, or alternatively inside the funnel mouth.

Because the pre-weakened line, i.e., the perforations 350, are formed through the entire thickness of the outer protective covering, sterility cannot be maintained within the specimen receptacle by the outer protective covering.

There is, therefore, provided an outer package 60, i.e., a closable container, for maintaining sterility within the interior of the specimen receptacle prior to use of the biological specimen collection and transport apparatus. The outer package 60 can be made of a translucent or transparent film if desired and encloses the base, hollow specimen receptacle, funnel, funnel lid, cap, and outer protective covering.

The outer package 60 is heat sealed at its top end 62 and bottom end 64 to close the top and bottom ends of the package.

It is desirable that means be provided to allow for passage of sterilizing fluids such as ethylene oxide gas into the closable container while preventing passage of microorganisms.

There can, for example, be slots or holes or the like formed in the translucent or transparent film which comprises such a closable container. A semi-permeable membrane can be bonded to the film completely covering the holes or slots. The semi-permeable membrane allows for passage of sterilizing fluids while prohibiting passage of microorganisms.

The outer package 60, shown in FIG. 5, comprises a polyethylene film in the form of a bag closed at both ends and having at least one slit 66 formed therein. The slit 66 is covered by a semi-permeable membrane in the form of a rectangular sterilization patch 68. The sterilization patch is bonded to the polyethylene bag by heat sealing or the like. The sterilization patch 68 allows for passage of a sterilizing fluid into the outer package 60 for sterilizing the specimen receptacle, while prohibiting the passage of microorganisms.

Various sizes and shapes of slits or holes can be used which require the use of various sizes and shapes of sterilization patches in order to maintain sterility within the container.

The outer protective covering 344 is used to maintain the exterior surface of the hollow specimen receptacle 12 free from being contaminated with a biological specimen during the specimen collection process in a similar manner as the outer protective covering 244 as shown in FIGS. 2 and 3. For example, it has been found that a sputum sample can flow down the outside surface of an outer protective covering such as the outer protective covering 344 having perforations formed therein without contaminating the outer surface of the specimen receptacle 12.

The use of the preferred embodiment, as shown in FIG. 5, can be desired, for example, when ease of separating the outer protective covering is desired or for other considerations such as aesthetics in packaging, manufacturing considerations, economic considerations, or the like.

In yet another preferred embodiment, as shown in FIG. 6, an outer protective covering 444 encloses the outer surface of the specimen receptacle 12 and the cap 26.

The outer protective covering can pass upwardly either between the specimen receptacle and the inner surface of the opening of the base 30 or it can pass outwardly around the base, enclosing the base.

The outer protective covering 444, shown in FIG. 6, passes upwardly between the base and the specimen receptacle 12 and is attached to the funnel 20. The means for attaching or sealing the outer protective covering 444 to the funnel 20 is a press fit provided between the outer surface of the discharge tube of the funnel 20 and the inner surface of the open top end 14 of the hollow specimen collection receptacle 12.

In the preferred embodiment, shown in FIG. 6, sterilization of the interior of the specimen receptacle 12 is not maintained by the outer protective covering 444 and, therefore, there is provided an outer package 160, i.e., a closable container, which can be made of a transparent or translucent film and which can be identical to the closable container, as described in the preferred embodiment shown in FIG. 5.

The outer protective covering 444 is used to maintain the specimen receptacle free of contamination during collection of the biological specimen and the outer package is provided to provide sterility during storage and transport prior to use of the apparatus, as described hereinabove.

Although this invention has been described in considerable detail with reference to certain versions thereof, it will be understood that variations and modifications can be effected within the spirit and scope of this invention described above and defined in the appended claims.

What is claimed is:

1. A biological specimen collection and transport apparatus which comprises:
   (a) an elongated hollow specimen receptacle having a closed bottom end and an open top end;
   (b) detachable conduit means for introducing a biological specimen into the hollow specimen receptacle mounted on the open end of the hollow specimen receptacle;
   (c) base means for receiving the closed bottom end of the elongated hollow specimen receptacle for supporting said elongated hollow specimen receptacle in a vertical position;
   (d) a flexible outer protective covering enclosing the outer surface of the elongated hollow specimen receptacle for preventing contamination of the outer surface of said elongated hollow specimen receptacle by a biological specimen during introduction of the biological specimen into said elongated hollow specimen receptacle; and
   (e) means for attaching the flexible outer protective covering to the detachable conduit means.

2. The biological specimen collection and transport apparatus according to claim 1 wherein the detachable conduit means comprises a funnel having a mouth at the top end and a discharge tube at the bottom end, wherein the outer surface of the discharge tube has a press fit within the open top end of the elongated hollow specimen receptacle.

3. The biological specimen collection and transport apparatus according to claim 2 including a funnel lid hingedly attached to the funnel for closing the mouth of said funnel.

4. The biological specimen collection and transport apparatus according to claim 3 wherein the funnel lid is hermetically sealed to the funnel.

5. The biological specimen collection and transport apparatus according to claim 2 wherein the means for attaching the flexible outer protective covering to the detachable conduit means comprises the press fit of the outer surface of the discharge tube within the open top end of the elongated hollow specimen receptacle.

6. The biological specimen collection and transport apparatus according to claim 1 wherein the means for attaching the flexible outer protective covering to the detachable conduit means is a bond between the flexible outer protective covering and the detachable conduit means.

7. The biological specimen collection and transport apparatus according to claim 1 wherein the means for attaching the flexible outer protective covering to the detachable conduit means is a hermetic seal.

8. The biological specimen collection and transport apparatus according to claim 7 wherein the hermetic seal comprises a heat seal.

9. The biological specimen collection and transport apparatus according to claim 1 wherein the flexible outer protective covering comprises an upper portion and a lower portion joined along a pre-weakened line located intermediate to the ends of said flexible outer protective covering.

10. The biological specimen collection and transport apparatus according to claim 1 wherein the flexible outer protective covering is comprised of a translucent plastic material.

11. The biological specimen collection and transport apparatus according to claim 10 wherein the translucent plastic material is comprised of polyethylene film.

12. The biological specimen collection and transport apparatus according to claim 1 wherein the flexible outer protective covering comprises means for passage of sterilizing fluids therethrough, while prohibiting passage of microorganisms.

13. The biological specimen collection and transport apparatus according to claim 12 wherein the means for passage of sterilizing fluids therethrough comprises a semi-permeable membrane.

14. The biological specimen collection and transport apparatus according to claim 1 wherein the hollow specimen receptacle is threaded at the open end and, additionally, a threaded cap is removably attached to the hollow specimen receptacle, the cap provided to engage the threads of the hollow specimen receptacle to provide a liquid seal between the cap and said specimen receptacle.

15. The biological specimen collection and transport apparatus according to claim 1 wherein the base means comprises a base comprising a hollow, generally hemispherically shaped enclosure having an opening in the center thereof for receiving the closed bottom end of said elongated hollow specimen receptacle in frictional engagement therein.

16. The biological specimen collection and transport apparatus according to claim 1 further comprising a closable container having the hollow specimen receptacle, detachable conduit means, base means, and flexible outer protective covering contained therein, wherein the closable container is sealed to maintain sterility of the hollow specimen receptacle.

17. A biological specimen collection and transport apparatus which comprises:
(a) an elongated, hollow specimen receptacle having a closed bottom end and an open top end;
(b) a funnel having a mouth at the top end and a discharge tube at the bottom end, wherein the outer surface of the discharge tube has a press fit within the open top end of the specimen receptacle;
(c) base means for receiving the closed bottom end of the elongated hollow specimen receptacle for supporting the receptacle in a vertical position; and
(d) a flexible outer protective covering enclosing the outer surface of the elongated hollow specimen receptacle, hermetically sealed to the funnel and comprising an upper portion and a lower portion joined along a score mark located intermediate the ends of the outer protective covering.

18. The biological specimen collection and transport apparatus according to claim 17 wherein such a score mark is provided at a location on the flexible outer protective covering between the funnel and the base means.

19. The biological specimen collection and transport apparatus according to claim 17 wherein such a score mark is generally transverse to the axis of the hollow specimen receptacle.

20. The biological specimen collection and transport apparatus as claimed in claim 17 wherein a first score mark is provided at a location on the flexible outer protective covering between the funnel and the base means and a second score mark is provided at a location on the flexible outer covering located above the first score mark and below the rim of the funnel.

21. The biological specimen collection and transport apparatus according to claim 17 wherein the flexible outer protective covering is comprised of a translucent plastic film.

22. The biological specimen collection and transport apparatus according to claim 21 wherein the translucent plastic film comprises polyethylene film.

23. The biological specimen collection and transport apparatus according to claim 17 wherein the flexible outer protective covering comprises means for passage of sterilizing fluids therethrough while prohibiting passage of microorganisms.

24. The biological specimen collection and transport apparatus according to claim 23 wherein the means for passage of sterilizing fluids therethrough comprises a semi-permeable membrane.

25. The biological specimen collection and transport apparatus according to claim 17 wherein the elongated hollow specimen receptacle is threaded at the open end and, additionally, a threaded cap is removably attached to the hollow specimen receptacle, the cap provided to engage the threads of the hollow specimen receptacle to provide a liquid seal between the cap and said hollow specimen receptacle.

26. The biological specimen collection and transport apparatus according to claim 17 additionally comprising a funnel lid, wherein said funnel lid is hingedly attached to the funnel for closing the mouth of the funnel and is hermetically sealed to the funnel.

27. A biological specimen collection and transport apparatus which comprises:
(a) an elongated hollow specimen receptacle having a closed bottom end and an open top end;
(b) a funnel having a mouth at the top and a discharge tube at the bottom end, wherein the outer surface of the discharge tube has a press fit within the open top end of the specimen receptacle;
(c) a base means for receiving the closed bottom end of the elongated hollow specimen receptacle for supporting said elongated hollow specimen receptacle in a vertical position;
(d) a flexible outer protective covering enclosing the elongated hollow specimen receptacle, base means and funnel, the flexible outer protective covering being attached to the funnel and comprising an upper portion and a lower portion joined along perforations located intermediate the ends of the outer protective covering; and
(e) a closable container having the hollow specimen receptacle, funnel, base means, and flexible outer protective covering contained therein, wherein the container is sealed to maintain sterility of the hollow specimen receptacle.

28. The biological specimen collection and transport apparatus according to claim 27 wherein the closable container comprises a transparent flexible material.

29. The biological specimen collection and transport apparatus according to claim 27 wherein such perforations are provided at a location on the flexible outer covering between the funnel and the base.

30. The biological specimen collection and transport apparatus according to claim 27 wherein the flexible outer protective covering is comprised of a translucent plastic film.

31. The biological specimen collection and transport system as claimed in claim 27 wherein the translucent plastic film comprises polyethylene film.

32. The biological specimen collection and transport apparatus according to claim 27 wherein the hollow specimen receptacle is threaded at the open end and, additionally, a threaded cap is removably attached to the hollow specimen receptacle, the cap provided to engage the threads of the hollow specimen receptacle to provide a liquid seal between the cap and said hollow specimen receptacle.

33. The biological specimen collection and transport system as claimed in claim 27 wherein the closable container additionally comprises a means for passage of sterilizing fluids therethrough, while prohibiting passage of microorganisms.

* * * * *

UNITED STATES PATENT AND TRADEMARK OFFICE
CERTIFICATE OF CORRECTION

PATENT NO. : 4,283,498

DATED : August 11, 1981

INVENTOR(S) : Joseph D. Schlesinger

It is certified that error appears in the above—identified patent and that said Letters Patent is hereby corrected as shown below:

Column 1, line 31, delete "a" and insert therefor -- an --. Column 14, line 13, delete "and" (first occurrence) and insert therefor -- end --.

Signed and Sealed this

Nineteenth Day of January 1982

[SEAL]

Attest:

Attesting Officer

GERALD J. MOSSINGHOFF

Commissioner of Patents and Trademarks